United States Patent [19]

Austel et al.

[11] 4,361,563

[45] Nov. 30, 1982

[54] PYRIDAZINONE-SUBSTITUTED BENZIMIDAZOLES AND SALTS

[75] Inventors: Volkhard Austel, Biberach; Joachim Heider, Warthausen; Wolfgang Eberlein, Biberach; Willi Diederen, Biberach; Walter Haarmann, Biberach, all of Fed. Rep. of Germany

[73] Assignee: Dr. Karl Thomae Gesellschaft mit Beschränkter Haftung, Biberach an der Riss, Fed. Rep. of Germany

[21] Appl. No.: 259,537

[22] Filed: May 1, 1981

Related U.S. Application Data

[63] Continuation-in-part of Ser. No. 65,605, Aug. 10, 1979, abandoned.

[30] Foreign Application Priority Data

Aug. 25, 1978 [DE] Fed. Rep. of Germany ....... 2837161
Jun. 1, 1979 [DE] Fed. Rep. of Germany ....... 2922336

[51] Int. Cl.³ .................. C07D 403/04; C07D 237/04; C07D 235/18; A61K 31/50
[52] U.S. Cl. .................................... 424/250; 544/238; 544/239; 549/329; 549/330; 549/332; 549/334; 549/325
[58] Field of Search .................... 424/250; 544/238

[56] References Cited

U.S. PATENT DOCUMENTS 4,026,891 3/1977 Austel ................................ 424/250

FOREIGN PATENT DOCUMENTS 54-16485 2/1979 Japan ................................... 544/238

*Primary Examiner*—Mark L. Berch
*Attorney, Agent, or Firm*—Hammond & Littell, Weissenberger & Muserlian

[57] ABSTRACT

Compounds of the formula

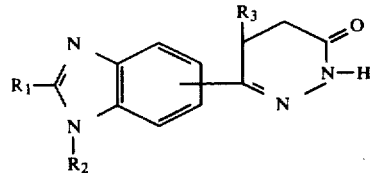

wherein $R_1$ is hydrogen; trifluoromethyl; alkyl of 1 to 11 carbon atoms; cycloalkyl of 3 to 7 carbon atoms; hydroxyl; alkoxy of 1 to 6 carbon atoms; mercapto; (alkyl of 1 to 6 carbon atoms)-mercapto; phenyl-(alkyl of 1 to 3 carbon atoms); phenyl; or mono-, di- or tri-substituted phenyl, where the substituents, which may be identical to or different from each other, are each halogen, alkyl of 1 to 4 carbon atoms, (alkyl of 1 to 6 carbon atoms)-sulfinyl, hydroxyl, alkoxy of 1 to 6 carbon atoms, mercapto or (alkyl of 1 to 6 carbon atoms)-mercapto;

$R_2$ is hydrogen, alkyl of 1 to 6 carbon atoms, cycloalkyl of 3 to 6 carbon atoms or phenyl-(alkyl of 1 to 3 carbon atoms); and $R_3$ is alkyl of 1 to 6 carbon atoms; optically active antipodes thereof; and non-toxic, pharmaceutically acceptable acid addition salts of said compounds or of said optically active antiposed. The compounds are useful as cardiotonics and antithrombotics.

10 Claims, No Drawings

PYRIDAZINONE-SUBSTITUTED BENZIMIDAZOLES AND SALTS

This is a continuation-in-part of copending application Ser. No. 65,605, filed Aug. 10, 1979, now abandoned.

This invention relates to novel pyridazinone-substituted benzimidazoles and non-toxic, pharmacologically acceptable acid addition salts thereof, to methods of preparing these compounds, to pharmaceutical compositions containing them as active ingredients, and to methods of using them as cardiotonics and antithrombotics.

More particularly the present invention relates to a novel class of compounds represented by the formula

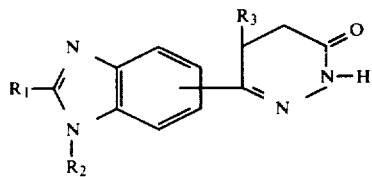

wherein
- $R_1$ is hydrogen; trifluoromethyl; alkyl of 1 to 11 carbon atoms; cycloalkyl of 3 to 7 carbon atoms; hydroxyl; alkoxy of 1 to 6 carbon atoms; mercapto; (alkyl of 1 to 6 carbon atoms)-mercapto; phenyl-(alkyl of 1 to 3 carbon atoms); phenyl; or mono, di- or trisubstituted phenyl, where the substituents, which may be identical to or different from each other, are each halogen, alkyl of 1 to 4 carbon atoms, (alkyl of 1 to 6 carbon atoms)-sulfinyl, hydroxyl, alkoxy of 1 to 6 carbon atoms, mercapto or (alkyl of 1 to 6 carbon atoms)-mercapto;
- $R_2$ is hydrogen, alkyl of 1 to 6 carbon atoms, cycloalkyl of 3 to 6 carbon atoms or phenyl-(alkyl of 1 to 3 carbon atoms); and
- $R_3$ is alkyl of 1 to 6 carbon atoms; optically active antipodes thereof;

and non-toxic, pharmaceutically acceptable acid addition salts of said compounds or of said optically active antipodes.

The benzimidazole group is substituted by the pyridazinone group in the 5- or 6-position.

Specific examples of substituents represented by $R_1$, $R_2$ and $R_3$ are the following:

$R_1$: Hydrogen, trifluoromethyl, methyl, ethyl, propyl, isopropyl, n-butyl, isobutyl, sec. butyl, tert. butyl, n-pentyl, 2-pentyl, tert. pentyl, isopentyl, n-hexyl, n-undecyl, cyclopropyl, cyclobutyl, cyclopentyl, cyclohexyl, cycloheptyl, hydroxyl, methoxy, ethoxy, propoxy, isopropoxy, mercapto, methylmercapto, ethylmercapto, propylmercapto, isopropylmercapto, hexylmercapto, benzyl, 1-phenylethyl, 2-phenylethyl, 1-phenylpropyl, 2-phenylpropyl, 1-phenyl-2-propyl, 3-phenylpropyl, phenyl, fluorophenyl, difluorophenyl, chlorophenyl, dichlorophenyl, bromophenyl, dibromophenyl, methylphenyl, dimethylphenyl, tert. butylphenyl, hydroxyphenyl, dihydroxyphenyl, methoxyphenyl, dimethoxyphenyl, trimethoxyphenyl, n-hexoxyphenyl, mercaptophenyl, dimercaptophenyl, methylmercaptophenyl, dimethylmercaptophenyl, methylsulfinylphenyl, dimethylsulfinylphenyl, fluorohydroxyphenyl, fluoromethoxyphenyl, fluoromercaptophenyl, fluoromethylmercaptophenyl, chlorohydroxyphenyl, chloromethoxyphenyl, chloromercaptophenyl, chloromethylmercaptophenyl, bromohydroxyphenyl, bromomethoxyphenyl, bromomercaptophenyl, bromomethylmercaptophenyl, hydroxymethoxyphenyl, hydroxymercaptophenyl, hydroxymethylmercaptophenyl, methoxymercaptophenyl, methoxymethylmercaptophenyl or methoxymethylsulfinylphenyl;

$R_2$: Hydrogen, methyl, ethyl, propyl, isopropyl, butyl, pentyl, isopentyl, cyclopropyl, cyclobutyl, cyclopentyl, cyclohexyl, benzyl, 1-phenylethyl, 2-phenylethyl or 3-phenylpropyl;

$R_3$: Methyl, ethyl, n-propyl, isopropyl, n-butyl, isobutyl, sec. butyl or tert. butyl.

A sub-genus thereunder is constituted by compounds of the formula I
wherein
- $R_1$ is hydrogen, trifluoromethyl; alkyl of 1 to 11 carbon atoms; cycloalkyl of 3 to 7 carbon atoms; hydroxyl; alkoxy of 1 to 6 carbon atoms; mercapto; (alkyl of 1 to 6 carbon atoms)-mercapto; phenyl-(alkyl of 1 to 3 carbon atoms); phenyl; hydroxyphenyl; halo-phenyl; (alkyl of 1 to 4 carbon atoms)-phenyl; (alkoxy of 1 to 6 carbon atoms)-phenyl; methoxy-halophenyl; methylmercapto-phenyl; methylsulfinyl-phenyl; dimethoxy-phenyl; methoxymethylmercapto-phenyl; methoxy-methylsulfinyl-phenyl; or trimethoxy-phenyl;
- $R_2$ is hydrogen, alkyl of 1 to 5 carbon atoms, cyclopropyl, cyclohexyl or benzyl; and
- $R_3$ is alkyl of 1 to 4 carbon atoms; optically active antipodes thereof; and non-toxic, pharmaceutically acceptable acid addition salts of said compounds or of said optically active antipodes.

A particularly preferred sub-genus is constituted by compounds of the formula I
wherein
- $R_1$ is hydrogen, methyl, 2-pentyl, cyclopropyl, 1-phenylethyl, ethoxy, methyl-mercapto, trifluoromethyl, phenyl, 4-methylphenyl, 2-fluoro-phenyl, 3-methoxy-phenyl, 4-methoxy-phenyl, 4-hexyloxyphenyl, or 4-hydroxy-phenyl;
- $R_2$ is hydrogen, 3-methyl-butyl, cyclopropyl or benzyl; and
- $R_3$ is methyl; optically active antipodes thereof; and non-toxic, pharmaceutically acceptable acid addition salts of said compounds or of said optically active antipodes.

An especially preferred sub-genus is constituted by compounds of the formula I
wherein
- $R_1$ is methyl, trifluoromethyl, 4-methyl-phenyl, 1-phenylethyl, 2-fluoro-phenyl, 3-methoxy-phenyl, 4-methoxy-phenyl or 4-hydroxy-phenyl;
- $R_2$ is hydrogen; and
- $R_3$ is methyl; optically active antipodes thereof; and non-toxic, pharmaceutically acceptable acid addition salts of said compounds of said optically active antipodes.

The novel substituted benzimidazoles of the present invention occur in the form of their racemates or of their optically active antipodes, based on the optically active carbon atoms in 5-position of the pyridazine ring.

The compounds of the present invention may be prepared by the following methods:

METHOD A

By cyclization of a compound, optionally prepared in the reaction mixture, of the formula

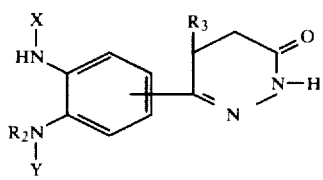
(II)

wherein

R$_2$ and R$_3$ are as defined above;

one of the radicals X or Y represents a hydrogen atom and the other of the radicals X or Y, or both of the radicals X and Y, represent a group of the formula

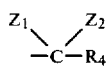
(III)

wherein

Z$_1$ and Z$_2$, which may be the same or different, each represent a hydroxyl group, a lower alkoxy group, an amino group, or a mercapto group, the amino or mercapto group being optionally substituted by a lower alkyl group, or Z$_1$ and Z$_2$ together represent an oxygen or sulfur atom or an imino group optionally substituted by an alkyl group having from 1 to 3 carbon atoms, or an alkylenedioxy or alkylenethio group, each group having 2 to 3 carbon atoms, and R$_4$ is as defined above for R$_1$ or, in addition, may represent an amino group optionally substituted by an alkyl group having from 1 to 3 carbon atoms, provided that if R$_4$ is a mercapto group, the group of the formula III represents an alkali metal salt thereof.

The cyclization is advantageously carried out in a suitable solvent, such as ethanol, isopropanol, glacial acetic acid, chlorobenzene, toluene, xylene, glycol, glycol monomethylether, diethyleneglycol dimethylether, dimethylformamide, ot tetraline, or in an excess of the acylating agent used for the preparation of the compound of the formula II, for example, in R$_1$CN, (R$_1$CO)$_2$O, R$_1$COOH, R$_1$CSOH or R$_1$CSSH or an ester, ortho ester, amide, halide or methoiodide thereof, at elevated temperatures, for example, at temperatures between about 0° and 250° C., Optionally, the cyclization is carried out in the presence of a condensation agent such as phosphorus oxychloride, thionyl chloride, sulfuryl chloride, sulfuric acid, hydrochloric acid, phosphoric acid, polyphosphoric acid, p-toluene sulfonic acid, glacial acetic acid or acetic acid anhydride, or also in the presence of a base such as potassium ethylate or potassium tert. butylate. However, the cyclization may also be carried out without a solvent and/or without a condensation agent.

The reaction is especially advantageously carried out by converting a 6-(acylamino-nitropheny)-pyridazine-3-one into a corresponding compound of the formula II by means of reduction, for example, by reduction with hydrogen in the presence of a hydrogenation catalyst such as Raney-nickel, platinum or palladium/charcoal; by reduction with metals such as iron, tin, or zinc; by reduction with metal salts such as iron (II)-sulfate, zinc (II)-chloride or chromo (II)-chloride; or by reduction with hydrazine in the presence of Raney-nickel. The compound of the formula II thus obtained can be cyclized in the same reaction mixture, if necessary in the presence of an acid such as hydrochloric acid, sulfuric acid, phosphoric acid, acetic acid, or a carboxylic acid of the formula R$_1$COOH, in the presence of a condensation agent such as phosphorus oxychloride, or in the presence of a base such as potassium ethylate, optionally in a solvent such as ethanol, isopropanol, glycol, dimethylformamide, dimethylsulfoxide or chlorobenzene, at temperatures between about 0° and 250° C.

For the preparation of a compound of the formula I wherein R$_1$ is mercapto, the compound is prepared in situ by reaction of a corresponding 7,8-diamino compound with carbon disulfide in the presence of an alkali metal alcoholate, e.g. in the presence of potassium ethylate, in an alcoholic solvent such as ethanol. The subsequent cyclization is effected by simple heating of the reaction mixture, preferably by heating to the boiling point of the reaction mixture.

METHOD B

By reaction of a carboxylic acid of the formula

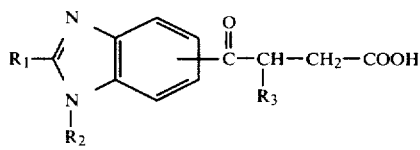
(IV)

wherein R$_1$, R$_2$, and R$_3$ are as defined above, or an ester, amide or halide thereof, with hydrazine.

The reaction is advantageously carried out in a solvent such as ethanol, isopropanol, glacial acetic acid, propionic acid and/or in an excess of hydrazine or hydrazine hydrate at elevated temperatures, for example, at temperatures between about 0° and 150° C., and optionally in the presence of an acid condensation agent, such as sulfuric acid or p-toluene sulfonic acid. The reaction may, however, also be carried out without a solvent.

A compound of the formula I, wherein R$_1$ represents a hydroxyl or mercapto group, or a phenyl group mono-, di or trisubstituted by a hydroxyl and/or mercapto group, and/or R$_2$ represents a hydrogen atom, can be converted by means of alkylation into a corresponding alkoxy, alkylmercapto and/or alkyl compound of the formula I. In addition, a compound of the formula I wherein R$_1$ represents a phenyl group substituted at least by one alkylmercapto group, can be converted by means of oxidation into a corresponding alkylsulfinylphenyl compound within the scope of formula I. Furthermore, a compound of the formula I wherein R$_1$ represents an alkylmercapto group, can be converted by means of oxidation and subsequent hydrolytic removal of the formed alkylsulfinyl or alkylsulfonyl group into a corresponding hydroxyl compound of the formula I. The above procedures of dehydrogenation, alkylation, etc. can be carried out either singly or successively.

The subsequent dehydrogenation is carried out with a dehydrogenation agent such as bromine, phosphorus pentachloride, sodium 3-nitro-benzene sulfonate, chromotrioxide, N-bromo-succinimide, hydrogen peroxide, or sodium nitrite in a solvent such as glacial acetic acid, propionic acid, water/glacial acetic acid, or nitrobenzene. The dehydrogenation is carried out at temperatures between about 0° and 100° C., preferably, however, at temperatures between about 50° and 80° C.

The subsequent alkylation is carried out with an alkylating agent such as an alkyl halide, dialkyl sulfate, trialkyl-oxonium-tetrafluoroborate, or diazoalkane, for example, with methyl iodide, dimethylsulfate, diethylsulfate, ethylbromide, or diazomethane, advantageously in a solvent such as methanol, ethanol, methanol/water, diethyl ether or dioxane, and optionally in the presence of a base such as sodium bicarbonate, sodium carbonate, sodium hydroxide, sodium methylate or potassium carbonate. The alkylation is carried out at temperatures up to the boiling point of the solvent which is used.

The subsequent oxidation is preferably carried out in a solvent such as glacial acetic acid or trifluoroacetic acid and appropriately with one equivalent of the oxidizing agent. If hydrogen peroxide is used as the oxidizing agent, an alkylsulfinylphenyl compound can be prepared. The oxidation is carried out at temperatures between about 0° and 50° C., but preferably at room temperature.

The racemic compounds of the formula I can be separated into their optically active antipodes. The separation is appropriately carried out by fractional crystallization of the corresponding salts with optically active acids such as tartaric acid, dibenzoyl tartaric acid, malic acid, camphoric acid, or camphor sulfonic acid.

Moreover, the compounds of the formula I or their optically active antipodes can be converted, if desired, into their physiologically compatible, i.e. non-toxic, pharmaceutically acceptable acid addition salts with inorganic or organic acids. Suitable acids include, for example, hydrochloric acid, hydrobromic acid, sulfuric acid, phosphoric acid, fumaric acid, succinic acid, lactic acid, citric acid, tartaric acid and maleic acid.

The starting compounds of the formulas II and IV can be obtained according to processes known from the art. See, for example British Pat. No. 1,466,547, incorporated herein by reference. Thus, a compound of the formula IV can be obtained, for example, by reaction of a compound of the formula

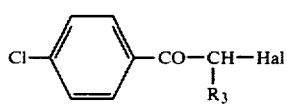 (V)

with malonic ester. The compound thus obtained is subsequently saponified, decarboxylated and nitrated, the chlorine atom is replaced by a corresponding amino group, the resulting compound is acylated, the nitro group is reduced, and the resulting compound is cyclized into the desired benzimidazole.

The compounds of the present application differ from those of British Pat. No. 1,466,547 by the alkyl substituent $R_3$ in the 5-position of the pyridazine ring. The new benzimidazoles surprisingly show a higher activity and/or a better oral absorption.

The new compounds of the present application show, in addition to a good oral absorption, superior pharmacological properties. While the compounds exhibit antiviral, interferon-inducing and ulcer-inhibiting activity, they especially exhibit cardiovascular activities, for example, cardiotonic, hypotensive and/or antithrombotic activities.

To demonstrate the remarkable activity of the invention herein, the following compounds A = 2-Methyl-5(6)-(5-methyl-3-oxo-4,5-dihydro-2H-6-pyridazinyl)-benzimidazole, B = 2-Trifluoromethyl-5(6)-(5-methyl-3-oxo-4,5-dihydro-2H-6-pyridazinyl)-benzimidazole, C = 5(6)-(5-Methyl-3-oxo-4,5-dihydro-2H-6-pyridazinyl)-benzimidazole, D = 2-(2-Fluoro-phenyl)-5(6)-(5-methyl-3-oxo-4,5-dihydro-2H-6-pyridazinyl)-benzimidazole, E = 2-(2,4-Dimethoxy-phenyl)-5(6)-(5-methyl-3-oxo-4,5-dihydro-2H-6-pyridazinyl)-benzimidazole, F = 2-Methylmercapto-5(6)-(5-methyl-3-oxo-4,5-dihydro-2H-6-pyridazinyl)-benzimidazole, G = 2-(4-Methoxy-phenyl)-5(6)-(5-methyl-3-oxo-4,5-dihydro-2H-6-pyridazinyl)-benzimidazole, H = 2-(4-Methyl-phenyl)-5(6)-(5-methyl-3-oxo-4,5-dihydro-2H-6-pyridazinyl)-benzimidazole, I = 2-(2-Pentyl)-5(6)-(5-methyl-3-oxo-4,5-dihydro-2H-6-pyridazinyl)-benzimidazole hydrochloride, K = 1-Methyl-2-(4-methoxy-phenyl)-5-(5-methyl-3-oxo-4,5-dihydro-2H-6-pyridazinyl)-benzimidazole, L = 1-(3-Methyl-butyl)-2-methyl-5-(5-methyl-3-oxo-4,5-dihydro-2H-6-pyridazinyl)-benzimidazole, and M = 1-Benzyl-2-methyl-5-(5-methyl-3-oxo-4,5-dihydro-2H-6-pyridazinyl)-benzimidazole were tested with regard to biological properties in comparison with the prior art compounds N = 2-Methyl-5(6)-(4-methyl-3-oxo-4,5-dihydro-2H-6-pyridazinyl)-benzimidazole, O = 2-(2,4-Dimethoxy-phenyl)-5(6)-(4-methyl-3-oxo-4,5-dihydro-2H-6-pyridazinyl)-benzimidazole, P = 2-(4-Methoxy-phenyl)-5(6)-(4-methyl-3-oxo-4,5-dihydro-2H-6-pyridazinyl)-benzimidazole and Q = 2-(4-Methoxy-phenyl)-5(6)-(2,4-dimethyl-3-oxo-4,5-dihydro-2H-6-pyridazinyl)-benzimidazole (see British Pat. No. 1,466,547).

TEST 1. DETERMINATION OF THE THROMBOCYTE AGGREGATION ACCORDING TO BORN AND CROSS [J. PHYSIOL. 170, 397 (1964)].

The thrombocyte aggregation was measured in platelet-rich plasma of healthy test persons. The decrease of the optical density was photometrically measured and recorded after addition of commercial collagen (Sigma, St. Louis, Mo., USA) which contained 1 ml of collagen-fibrils per ml. The velocity of aggregation (Vmax) was determined by the angle of inclination of the density curve. The point of the curve, where the most light was transmitted, served for the determination of the optical density (o.d.). To provoke maximum aggregation, approximately 0.01 ml of the collagen solution was added to 1 ml of platelet-rich plasma.

The test results are set forth in the following table:

TABLE I

| Compound | $EC_{50}$ in μMol/liter |
| --- | --- |
| Invention: | |
| A | 0.01 |
| B | 0.1 |
| C | 0.12 |
| G | 0.08 |
| L | 0.05 |
| Prior art: | |
| N | 1.0 |

TEST 2. DETERMINATION OF THE HYPOTENSIVE AND POSITIVE INOTROPIC ACTIVITY IN THE CAT

The tests were performed in cats which were anesthetized with pentobarbital sodium (40 mg/kg i.p.). The animals breathed spontaneously. The arterial blood pressure was measured in the aorta abdominalis by a Statham pressure transducer (P 23 Dc). The positive inotropic effect was determined by measuring the pressure in the left auricle by means of a catheter tipmanometer (Millar PC 350 A). This contractility parameter $dp/dt_{max}$ was registered by means of an analog differentiating circuit. The substances under test were injected into a vena femoralis. Physiological sodium hydrochloride solution or polydiol 200 was used as solvent. Each substance was tested in at least 3 cats, dose 0.1, 0.5 or 2.0 mg/kg i.v. The test substances showed an activity of at least 1 hour.

The following table sets forth the average values:

TABLE II

| Compound | Dose mg/kg i.v. | Change of blood pressure mgm Hg | Change of dp/dt in % | Duration of action in minutes |
|---|---|---|---|---|
| Invention: | | | | |
| A | 0.1 | −26/−24 | +53 | >24 |
| A | 0.5 | −35/−42 | +116 | >187 |
| B | 0.1 | −65/−35 | +91 | >55 |
| B | 0.5 | −49/−43 | +143 | >99 |
| C | 0.5 | −55/−48 | +159 | >172 |
| D | 0.5 | −8/−10 | +107 | >69 |
| E | 0.5 | −28/−33 | +89 | >55 |
| F | 0.1 | −36/−40 | +51 | >28 |
| F | 0.5 | −48/−66 | +50 | >32 |
| G | 0.1 | +3/0 | +23 | >26 |
| G | 0.5 | −18/−18 | +64 | >72 |
| H | 0.5 | −10/−10* | +118 | >69 |
| I | 0.1 | −10/−13 | +83 | >53 |
| I | 0.5 | −28/−33 | +103 | >52 |
| K | 0.5 | −28/−34 | +50 | >40 |
| M | 0.1 | −37/−33 | +123 | >62 |
| M | 0.5 | −57/−48 | +106 | >110 |
| Prior art: | | | | |
| N | 0.5 | +5/3 | +23 | 22 |
| O | 0.5 | +15/6 | +10 | 2 |
| P | 0.5 | −10/−10 | +9 | 1 |
| P | 2.0 | −35/−35 | +5 | 1 |
| Q | 0.5 | −12/−12 | −16 | 11 |
| Q | 2.0 | −40/−4− | −26 | 3 |

*initial increase of blood pressure (33/18); after 1 minute decrease of blood pressure, duration: >50 minutes.

TEST 3. ACUTE TOXICITY

The acute toxicity of the substances tested was determined in white mice after oral adminstration of a single dose (observation time: 14 days). The results are set forth in the following table:

TABLE III

| Compound | Acute toxicity mg/kg p.o. |
|---|---|
| Invention: | |
| A | >600 (1 out of 3 animals died) |
| B | >450 (0 out of 6 animals died) |
| D | >600 (0 out of 6 animals died) |
| G | ~600 (3 out of 6 animals died) |
| H | >600 (0 out of 6 animals died) |
| Prior art: | |
| N | >250 (0 out of 10 animals died) |

According to their pharmacological properties, the compounds of general formula I prepared according to the invention, and the optically active antipodes thereof as well as their physiologically compatible acid addition salts with inorganic or organic acids, are suitable in the treatment of chronic cardiac insufficiency or angina pectoris and/or for the prophylaxis of arterial thromboemboli and diseases of arterial occlusion. They are also useful in the treatment of ulcers and in combatting viruses and viral diseases.

The novel substituted benzimidazoles can be incorporated into conventional pharmaceutical preparations, optionally in combination with other active ingredients. Preferred forms include tablets, coated tablets, powder, suppositories, suspensions, ampules, or drops. A single dose comprises from about 5 to 200 mg, i.e. from about 0.08 to 3.33 mg/kg, of a compound of the invention, administered from one to four times daily. Preferably a single dose comprises from about 15 to 150 mg, i.e. from about 0.25 to 2.5 mg/kg, one to four times daily.

Since the compounds of the formula I may exist in their tautomeric form 1H or 3H, the point of substitution on the benzimidazole nucleus is designated with 5(6).

The following examples serve to illustrate the invention and are not to be construed as limiting the invention thereto.

EXAMPLE 1

2-(4-Methoxy-phenyl)-5(6)-(5-methyl-3-oxo-4,5-dihydro-2H-6-pyridazinyl)-benzimidazole hydrochloride (a) 3-[3-Nitro-4-(4-methoxy-benzoylamino)-benzoyl]-butyric acid methyl ester A mixture of 10 gm of 3-(3-nitro-4-amino-benzoyl)-butyric acid methyl ester and 10.2 gm of 4 aniseed acid chloride in 100 ml of chlorobenzene was refluxed until the complete reaction of the 3-(3-nitro-4-amino-benzoyl)-butyric acid methyl ester was reached. The reaction mixture was stirred with activated charcoal and filtered, and the filtrate was mixed with cyclohexane, whereby the product was obtained as crystals. The crystals were suction filtered and washed with cyclohexane and petroleum ether.

Yield: 10.7 gm (73% of theory).

M.p.: 107°–117° C.

(b) 5-Methyl-6-[3-nitro-4-(4-methoxy-benzoylamino)-phenyl]-3-oxo-4,5-dihydro-2H-pyridazine 20 ml of 80% hydrazine hydrate were added dropwise to 150 ml of glacial acetic acid while stirring and ice cooling. After cooling, 10.7 gm of 3-[3-nitro-4-(4-methoxybenzoylamino)-benzoyl]-butyric acid methyl ester were added and the mixture was refluxed for 40 minutes. After cooling, 250 ml of ice water were added, and the precipitate formed was suction filtered and washed with ice water.

Yield: 9.8 gm (96% of theory).

M.p.: 219° C.

(c) 5-Methyl-6-[3-amino-4-(4-methoxy-benzoylamino)phenyl]-3-oxo-4,5-dihydro-2H-pyridazine 9.8 gm of 5-methyl-6-[3-nitro-4-(4-methoxy-benzoylamino)-phenyl]-3-oxo-4,5-dihydro-2H-pyridazine were dissolved in 1000 ml of ethanol and hydrogenated for 24 hours at room temperature with a hydrogen pressure of 5 bar in the presence of 1 gm of 10% palladium charcoal. The obtained precipitate was suction filtered and used in the next step without removing the catalyst. A further fraction of the product can be obtained from the mother liquors.

Yield: 8.5 gm (94.4% of theory).

(d) 2-(4-Methoxy-phenyl)-5(6)-(5-methyl-3-oxo-4,5-dihydro-2H-6-pyridazinyl)-benzimidazole-hydrochloride The product obtained according to the method described in (c) was refluxed in 100 ml of glacial acetic acid for 1.5 hours and the hot reaction mixture was filtered through a glass frit. 100 gm of ice were added to the filtrate, and the orange-yellow precipitate that formed was filtered off and washed with dilute acetic acid. The united filtrates were made alkaline by means of ammonia. The precipitated product, obtained in crystalline form, was suction-filtered and purified on a silicagel column (eluting agent: methylene chloride/ethanol = 50:1 and 25:1). The hydrochloride was precipitated from methanol with ethereal hydrochloric acid.

Yield: 4.45 gm (49.8% of theory).

M.p.: 311° C. (decomp.).

EXAMPLE 2

2-(4-Methoxy-phenyl)-5(6)-(5-methyl-3-oxo-4,5-dihydro-2H-pyridazinyl)-benzimidazole hydrochloride (a) 2-(4-Methoxy-phenyl-5(6)-(1-oxo-2-methyl-3-methoxycarbonyl-1-propyl)-benzimidazole hydrochloride 9.2 gm of 5-methyl-6-[3-nitro-4-(4-methoxy-benzoylamino)-phenyl]-3-oxo-4,5-dihydro-2H-pyridazine were hydrogenated in a mixture of 300 ml of methanol and 3 ml of glacial acetic acid for 2.5 hours at room temperature with a hydrogen pressure of 5 bar and in the presence of 2 gm of 10% palladium charcoal. Hydrogen chloride gas was introduced to the reaction mixture for 2.5 hours while refluxing. The reaction mixture was then mixed with ether and the product obtained was suction-filtered and washed with ether.

Yield: 4.5 gm (50.5% of theory).

M.p.: above 300° C.

(b) 2-(4-Methoxy-phenyl)-5(6)-(5-methyl-3-oxo-4,5-dihydro-2H-6-pyridazinyl)-benzimidazole hydrochloride 1 ml of 80% hydrazine hydrate was dissolved in 10 ml of glacial acetic acid, and, after cooling, 0.43 gm of 2-(4-methoxy-phenyl)-5(6)-(1-oxo-2-methyl-3-methoxycarbonyl-1-propyl)-benzimidazole hydrochloride were added. The precipitated prodict was suction-filtered, washed with water, and purified over a silicagel column (eluting agent: chloroform/methanol = 50.1). The hydrochloride was precipitated from ethanol with ethereal hydrochloric acid.

Yield: 0.3 gm (70.3% of theory).

M.p.: 314° C. (decomp.).

EXAMPLE 3

2-Methyl-5(6)-(5-methyl-3-oxo-4,5-dihydro-2H-6-pyridazinyl)benzimidazole hydrochloride 29 gm of 5-methyl-6-(3-nitro-4-acetamino-phenyl)-3-oxo-4,5-dihydro-2H-pyridazine were hydrogenated in a mixture of 1200 ml of methanol and 100 ml of glacial acetic acid for 2.5 hours at room temperature with a hydrogen pressure of 5 bar in the presence of 5 gm of 10% palladium charcoal. The catalyst was filtered off and the filtrate was evaporated. The residue was dissolved in 400 ml of glacial acetic acid, and the solution was heated at 100° C. for 40 minutes. The reaction mixture was poured on 1 liter of ice and while cooling adjusted to pH 8 by addition of concentrated ammonia. The precipitated free base was subsequently converted into the hydrochloride by dissolution in methanol and addition of ethereal hydrochloric acid.

Yield: 19.7 gm (70.7% of theory).

M.p.: 308° C.

EXAMPLE 4

2-(2,4-Dimethoxy-phenyl)-5(6)-(5-methyl-3-oxo-4,5-dihydro-2H-6-pyridazinyl)-benzimidazole hydrochloride (a) 2-(2,4-Dimethoxy-phenyl)-5(6)-(1-oxo-2-methyl-3-ethoxycarbonyl-1-propyl)-benzimidazole hydrochloride Prepared analogous to Example 2(a) from 12.2 gm of 5-methyl-6-[3-nitro-4-(2,4-dimethoxy-benzoylamino)-phenyl]-3-oxo-4,5-dihydro-2H-pyridazine. The imidazole ring was closed with ethanolic hydrochloric acid. The product was roughly purified and processed further in this form.

Yield: 4 gm (31.2% of theory).

(b) 2-(2,4-Dimethoxy-phenyl)-5(6)-(5-methyl-3-oxo-4,5-dihydro-2H-6-pyridazinyl)-benzimidazole hydrochloride Prepared analogous to Example 2(b) from the product obtained according to Example 4(a).

Yield: 0.78 gm (21.1% of theory).

M.p.: 266° C.

EXAMPLE 5

2-(4-Methyl-phenyl)-5(6)-(5-methyl-3-oxo-4,5-dihydro-2H-6-pyridazinyl)-benzimidazole hydrochloride Prepared analogous to Example 2(b) from 1.5 gm of 2-(4-methyl-phenyl)-5(6)-(1-oxo-2-methyl-3-methoxycarbonyl-1-propyl)-benzimidazole hydrochloride.

Yield: 0.24 gm (16.5% of theory).

M.p.: 340° C. (decomp.).

EXAMPLE 6

2-(4-Methyl-phenyl)-5(6)-(5-methyl-3-oxo-4,5-dihydro-2H-6-pyridazinyl)-benzimidazole hydrochloride Prepared analogous to Example 1(d) from 21.5 gm of 5-methyl-6-[2-amino-4-(4-methyl-benzoylamino)-phenyl]-3-oxo-4,5-dihydro-2H-pyridazine. (A chromatographic purification was not necessary).

Yield: 18.8 gm (82.7% of theory).

M.p.: 340° C. (decomp.).

EXAMPLE 7

2-Cyclopropyl-5(6)-(5-methyl-3-oxo-4,5-dihydro-2H-6-pyridazinyl)-benzimidazole hydrochloride Prepared analogous to Example 6 from 2.3 gm of 5-methyl-6-(3-nitro-4-cyclopropylcarbonylamino-phenyl)-3-oxo-4,5-dihydro-2H-pyridazine.

Yield: 1.35 gm (61.2% of theory).

M.p.: 235°–237° C. (decomp.).

EXAMPLE 8

1,2-Dimethyl-5(6)-(5-methyl-3-oxo-4,5-dihydro-2H-6-pyridazinyl)-benzimidazole (a) 5-Methyl-6-(3-amino-4-acetyl-methylamino-phenyl)-3-oxo-4,5-dihydro-2H-pyridazine 0.65 gm of 5-methyl-6-(3-nitro-4-acetyl-methylamino-phenyl)-3-oxo-4,5-dihydro-2H-pyridazine were dissolved in 30 ml of ethanol and mixed with 0.5 ml of 80% hydrazine hydrate and 0.5 gm of Raney-nickel. The reaction mixture was heated at 30° C. for 10 minutes. After filtering off of the catalyst, the filtrate was mixed with glacial acetic acid and evaporated in vacuo. The residue was directly processed further.

(b) 1,2-Dimethyl-5(6)-(5-methyl-3-oxo-4,5-dihydro-2H-6-pyridazinyl)-benzimidazole Prepared analogous to Example 1(d) from the product obtained according to Example 8(a).

Yield: 0.15 gm (27.4% of theory).
M.p.: above 250° C.

EXAMPLE 9

2-(2-Fluoro-phenyl)-5(6)-(5-methyl-3-oxo-4,5-dihydro-2H-6-pyridazinyl)-benzimidazole hydrochloride 3.2 gm of 5-methyl-6-[3-amino-4-(2-fluoro-benzoylamino)-phenyl]-3-oxo-4,5-dihydro-2H-pyridazine were suspended in 150 ml of isopropanol, and hydrogen chloride gas was introduced into the mixture while refluxing for 2 hours. After evaporation the residue was triturated with ether, whereby the end product was obtained in crystalline form.

Yield: 1.35 gm (40% of theory).
M.p.: 295° C.

EXAMPLE 10

2-Phenyl-5(6)-(5-methyl-3-oxo-4,5-dihydro-2H-6-pyridazinyl)-benzimidazole hydrochloride Prepared analogous to Example 9 from 2.0 gm of 5-methyl-6-(3-amino-4-benzoylamino-phenyl)-3-oxo-4,5-dihydro-2H-pyridazine.

Yield: 0.85 gm (40.5% of theory).
M.p.: 335° C.

EXAMPLE 11

2-Isopropyl-5(6)-(5-methyl-3-oxo-4,5-dihydro-2H-6-pyridazinyl)-benzimidazole hydrochloride Prepared analogous to Example 9 from 6.2 gm of 5-methyl-6-(3-amino-4-isobutyrylamino-phenyl)-3-oxo-4,5-dihydro-2H-pyridazine.

Yield: 4.7 gm (71% of theory).
M.p.: 270°–272° C.

EXAMPLE 12

2-n-Pentyl-5(6)-(5-methyl-3-oxo-4,5-dihydro-2H-6-pyridazinyl)-benzimidazole hydrochloride Prepared analogous to Example 9 from 1.8 gm of 5-methyl-6-(3-amino-4-caproylamino-phenyl)-3-oxo-4,5-dihydro-2H-pyridazine.

Yield: 0.8 gm (41.8% of theory).
M.p.: 244° C.

EXAMPLE 13

2-(4-Chloro-phenyl)-5(6)-(5-methyl-3-oxo-4,5-dihydro-2H-6-pyridazinyl) benzimidazole Prepared analogous to Example 2(b) from 1.45 gm of 2-(4-chloro-phenyl)-5(6)-(1-oxo-2-methyl-3-methoxycarbonyl-1-propyl)-benzimidazole hydrochloride.

Yield: 0.32 gm (23% of theory).
M.p.: sintering from 78° C.

EXAMPLE 14

2-Trifluoromethyl-5(6)-(5-methyl-3-oxo-4,5-dihydro-2H-6-pyridazinyl)-benzimidazole 11 gm of 5-methyl-6-(3,4-diamino-phenyl)-3-oxo-4,5-dihydro-2H-pyridazine were refluxed with 70 ml of trifluoroacetic acid for 2 hours. The reaction mixture was evaporated in vacuo, mixed with ice water, and made alkaline with ammonia. After extraction with ethyl acetate, the ethyl acetate phases were evaporated and the residue was recrystallized from 50% ethanol in the presence of activated charcoal.

Yield: 6.4 gm (50% of theory).
M.p.: 278°–280° C.

EXAMPLE 15

5(6)-(5-methyl-3-oxo-4,5-dihydro-2H-6-pyridazinyl)-benzimidazole hydrochloride

Prepared analogous to Example 14 from 2.0 gm of 5-methyl-6-(3,4-diaminophenyl)-3-oxo-4,5-dihydro-2H-pyridazine and formic acid. The hydrochloride was precipitated from methanol with ethereal hydrochloric acid and recrystallized from ethanol/ether.

Yield: 0.6 gm (28.9% of theory).
M.p.: 300° C. (decomp.).

EXAMPLE 16

2-Mercapto-5(6)-(5-methyl-3-oxo-4,5-dihydro-2H-6-pyridazinyl)-benzimidazole 5.2 gm of potassium hydroxide were dissolved in a mixture of 50 ml of ethanol and 6.6 ml of water. 3.84 gm of carbon disulfide and 11.0 gm of 5-methyl-6-(3,4-diaminophenyl)-3-oxo-4,5-dihydro-2H-pyridazine were then added, and the mixture was refluxed for 3 hours. After dilution with water, the reaction mixture was neutralized with glacial acetic acid. The precipitated product was suction-filtered and washed with water.

Yield: 10.6 gm of crude product (94.3% of theory). The product was purified on a silicagel column (eluting agent: chloroform/ethanol = 9:1).

M.p.: above 300° C.

EXAMPLE 17

2-Methylmercapto-5(6)-(5-methyl-3-oxo-4,5-dihydro-2H-6-pyridazinyl)-benzimidazole 6.0 gm of the crude product obtained according to Example 16 were dissolved in 250 ml of dimethylformamide. Subsequently, 3.3 gm of methyl iodide and 1.4 gm of sodium bicarbonate were added. The mixture was stirred for 1 hour at room temperature and for 1 hour at 50° C. The solvent was removed in vacuo. The residue was triturated with water and purified on a silicagel column.

Yield: 1.5 gm (23.8% of theory).
M.p.: 268° C. (decomp.).

EXAMPLE 18

2-Cyclohexyl-5(6)-(5-methyl-3-oxo-4,5-dihydro-2H-6-pyridazinyl)-benzimidazole hydrochloride Prepared analogous to Example 1(c) and 1(d) from 9.7 gm of 5-methyl-6-(3-nitro-4-cyclohexylcarbonylamino-phenyl)-3-oxo-4,5-dihydro-2H-pyridazine. The hydrochloride was precipitated from acetone with ethereal hydrochloric acid and recrystallized from ethanol.

Yield: 2.3 gm (24.7% of theory).
M.p.: 315°–320° C.

EXAMPLE 19

2-(4-tert.Butyl-phenyl)-5(6)-(5-methyl-3-oxo-4,5-dihydro-2H-6-pyridazinyl)-benzimidazole hydrochloride hydrate (a) 5-Methyl-6-[3-amino-4-(4-tert.butyl-benzoylamino)phenyl]-3-oxo-4,5-dihydro-2H-pyridazine Prepared analogous to Example 1(c) from 12.6 gm of 5-methyl-6-[3-nitro-4-(4-tert.butyl-benzoyl-amino)-phenyl]-3-oxo-4,5-dihydro-2H-pyridazine. After filtering off the catalyst, the product was precipitated with water.

Yield: 9.9 gm (84.5% of theory).
M.p.: 215°–217° C.

(b) 2-(4-tert.Butyl-phenyl)-5(6)-(5-methyl-3-oxo-4,5-dihydro-2H-6-pyridazinyl)-benzimidazole hydrochloride hydrate Prepared analogous to Example 1(d) from the product obtained according to Example 19(a).

Yield: 7.9 gm (73% of theory).
M.p.: 294°–298°.

EXAMPLE 20

2-(2-Pentyl)-5(6)-(5-methyl-3-oxo-4,5-dihydro-2H-6-pyridazinyl)-benzimidazole hydrochloride (a) 5-Methyl-6-[3-amino-4-(2-methyl-valeryl-amino)-phenyl]-3-oxo-4,5-dihydro-2H-pyridazine Prepared analogous to Example 19(a) from 12.5 gm of 5-methyl-6-[3-nitro-4-(2-methyl-valeryl-amino)-phenyl]-3-oxo-4,5-dihydro-2H-pyridazine. After mixing with water, the product was extracted with ethyl acetate.

Yield: 4.2 gm (36.6% of theory).
M.p.: 179°–181° C.

(b) 2-(2-Pentyl)-5(6)-(5-methyl-3-oxo-4,5-dihydro-2H-6-pyridazinyl benzimidazole) hydrochloride Prepared analogous to Example 1(d) from the product obtained according to Example 20(a).

Yield: 1.3 gm (28.4% of theory).
M.p.: sintering from 150° C.

EXAMPLE 21

2-(n-Hexyl)-5(6)-(5-methyl-3-oxo-4,5-dihydro-2H-6-pyridazinyl)-benzimidazole hydrochloride (a) 5-Methyl-6-(3-amino-4-heptanoyl-amino-phenyl)-3-oxo-4,5-dihydro-2H-pyridazine Prepared analogous to Example 19(a) from 11.75 gm of 5-methyl-6-(3-nitro-4-heptanoyl-amino-phenyl)-3-oxo-4,5-dihydro-2H-pyridazine.

Yield: 8.0 gm (78% of theory).
M.p.: 158°–160° C.

(b) 2-(n-Hexyl)-5(6)-(5-methyl-3-oxo-4,5-dihydro-2H-6-pyridazinyl)-benzimidazole hydrochloride Prepared analogous to Example 1(d) from the product obtained according to Example 21(a).

Yield: 6.2 gm (73.5% of theory).
M.p.: 225°–227° C.

EXAMPLE 22

1-Cyclohexyl-2-methyl-5(6)-(5-methyl-3-oxo-4,5-dihydro-2H-6-pyridazinyl)-benzimidazole 1.3 gm of 5-methyl-6-(3-amino-4-cyclohexylamino-phenyl)-3-oxo-4,5-dihydro-2H-pyridazine were refluxed with 50 ml of glacial acetic acid for 6 hours. The reaction mixture was poured on ice, neutralized with ammonia and the product which precipitated was purified on a silicagel column (eluting agent: methylene chloride/aceton = 10:0 to 9:1).

Yield: 0.4 gm (28.5% of theory).
M.p.: 259°–262° C. (decomp.).

EXAMPLE 23

2-Hydroxy-5(6)-(5-methyl-3-oxo-4,5-dihydro-2H-6-pyridazinyl)-benzimidazole 2 gm of 2-methylmercapto-5(6)-(5-methyl-3-oxo-4,5-dihydro-2H-6-pyridazinyl)-benzimidazole were dissolved in 100 ml of glacial acetic acid. 10 ml of 30% hydrogen peroxide were added, and the mixture was heated at 50° C. for 6 hours. After 3 and 4 hours each, 2 ml of hydrogen peroxide were added. The reaction mixture was largely evaporated in vacuo and then poured into water, and the resulting precipitate was recrystallized from ethanol/cyclohexane.

Yield: 0.37 gm (21% of theory).
M.p. above 300° C.

EXAMPLE 24

2-(2-Methoxy-4-methylmercapto-phenyl)-5(6)-(5-methyl-3-oxo-4,5-dihydro-2H-6-pyridazinyl)-benzimidazole 2.5 gm of 5-methyl-6-[3-amino-4-(2-methoxy-4-methylmercapto-benzoyl-amino)-phenyl]-3-oxo-4,5-dihydro-2H-pyridazine were refluxed in 100 ml of glacial acetic acid for 2.5 hours. The reaction mixture was filtered while hot, and after cooling it was added while stirring to a mixture of ice and concentrated ammonia. After drying of the precipitated product, it was recrystallized from methylene chloride.

Yield: 1.1 gm (57.7% of theory).
M.p.: 155°–165° C. (decomp.).

EXAMPLE 25

1-Cyclopropyl-2-methyl-5(6)-(5-methyl-3-oxo-4,5-dihydro-2H-6-pyridazinyl)-benzimidazole (a) 5-Methyl-6-(3-amino-4-cyclopropylamino-phenyl)-3-oxo-4,5-dihydro-2H-pyridazine 5.8 gm of 5-methyl-6-(3-nitro-4-cyclopropylamino-phenyl)-3-oxo-4,5-dihydro-2H-pyridazine were hydrogenated in a mixture consisting of 100 ml of ethanol and of 20 ml of glacial acetic acid in the presence of 0.5 gm of 10% palladium charcoal at a hydrogen pressure of 5 bar. 120 ml of glacial acetic acid were added, the catalyst was filtered off and the filtrate was evaporated in vacuo. The residue was reacted further without further purification.

(b) 1-Cyclopropyl-2-methyl-5(6)-(5-methyl-3-oxo-4,5-dihydro-2H-6-pyridazinyl)-benzimidazole Prepared analogous to Example 22 from the product obtained according to Example 25(a) and 30 ml of glacial acetic acid (duration of heating: 3 hours, column-chromatographic purification not necessary).

Yield: 4.6 gm (81.5% of theory).
M.p.: 246°–250° C.

EXAMPLE 26

2-Hexylmercapto-5(6)-(5-methyl-3-oxo-4,5-dihydro-2H-6-pyridazinyl)-benzimidazole Prepared analogous to Example 17 from 2.6 gm of 2-mercapto-5(6)-(5-methyl-3-oxo-4,5-dihydro-2H-6-pyridazinyl)-benzimidazole and 1.7 gm of 1-bromohexane (reaction temperature: 80° C., reaction time: 7 hours).

Yield: 1.0 gm (29% of theory).
M.p.: 172° C. (decomp. from isopropanol/petroleum ether).

EXAMPLE 27

1-Methyl-2-(4-methoxy-phenyl)-5-(5-methyl-3-oxo-4,5-dihydro-2H-6-pyridazinyl)-benzimidazole A mixture of 6.4 gm of 5-methyl-6-{3-nitro-4-[N-methyl-(4-methoxy-benzoyl)-amino]-phenyl}-4,5-dihydro-2H-pyridazine-3-one and 0.6 gm of 10% palladium charcoal in 100 ml of ethanol was treated for 2.5 hours at room temperature with hydrogen at 5 bar. The catalyst was suction filtered off, and the filtrate was evaporated in vacuo. The residue was purified by chromatography on silicagel (eluting agent: methylene chloride/ethanol 19:1 to 9:1). The corresponding fractions were evaporated and the product was crystallized by trituration with ether.

Yield: 0.15 gm (3% of theory).
M.p.: 248°-249° C.

EXAMPLE 28

1-Benzyl-2-methyl-5-(5-methyl-3-oxo-4,5-dihydro-2H-6-pyridazinyl)-benzimidazole (a) 5-Methyl-6-(3-amino-4-benzylamino-phenyl)-4,5-dihydro-2H-pyridazine-3-one A mixture of 6.75 gm of 5-methyl-6-(3-nitro-4-benzylamino-phenyl)-4,5-dihydro-2H-pyridazine-3-one and 0.7 gm of 10% palladium charcoal in a mixture of 100 ml of ethanol and 20 ml of glacial acetic acid was treated for 3.5 hours at room temperature with hydrogen at 5 bar. The catalyst was filtered off, the filtrate was evaporated, and the residue was used in the next step without further purification.

(b) 1-Benzyl-2-methyl-5-(5-methyl-3-oxo-4,5-dihydro-2H-6-pyridazinyl)-benzimidazole The product obtained according to (a) was taken up in 100 ml of glacial acetic acid and refluxed for 2.5 hours. The mixture was mixed with ice and made alkaline with ammonia, and the precipitated product was purified by chromatography on silicagel (eluting agent: at first pure methylene chloride, then increasing amounts of acetone up to a mixture ratio methylene chloride/acetone=10:3). After evaporation, the product was obtained in crystalline form by trituration with ether.

Yield: 2.2 gm (33% of theory).
M.p.: 279° C.

EXAMPLE 29

1-Cyclohexyl-2-methyl-6-(5-methyl-3-oxo-4,5-dihydro-2H-6-pyridazinyl)-benzimidazole Prepared analogous to Example 28 from 1.3 gm of 5-methyl-6-(3-amino-4-cyclohexylamino-phenyl)-4,5-dihydro-2H-pyridazine-3-one. After separation of 1-cyclohexyl-2-methyl-5-(5-methyl-3-oxo-4,5-dihydro-2H-6-pyridazinyl)-benzimidazole by chromatography on silicagel (eluting agent: methylene chloride/acetone=10:0 to 9:1), the product was obtained in pure form.

Yield: 0.1 gm (7% of theory).
M.p.: 237° C. (decomp.).

EXAMPLE 30

2-Isopropylmercapto-5(6)-(5-methyl-3-oxo-4,5-dihydro-2H-6-pyridazinyl)-benzimidazole 3.4 gm of 2-mercapto-5(6)-(5-methyl-3-oxo-4,5-dihydro-2H-6-pyridazinyl)-benzimidazole were dissolved in 50 ml of dimethylformamide. 1.62 gm of isopropyl bromide and 1.1 gm of sodium bicarbonate were added, and the mixture was stirred for 20 hours on a steam bath. The solvent was evaporated in vacuo, and the residue was purified by chromatography on silicagel (eluting agent: chloroform/ethanol 9:1).

Yield: 0.45 gm (11% of theory).
M.p. 120°-121° C.

EXAMPLE 31

2-(2-Methoxy-4-methylsulfinyl-phenyl)-5(6)-(5-methyl-3-oxo-4,5-dihydro-2H-6-pyridazinyl)-benzimidazole 0.9 gm of 2-(2-methoxy-4-methylmercapto-phenyl)-5(6)-(5-methyl-3-oxo-4,5-dihydro-2H-6-pyridazinyl)-benzimidazole were dissolved in 50 ml of glacial acetic acid, and a solution of 0.24 gm of 30% hydrogen peroxide in 10 ml of glacial acetic acid was added. After standing for 22 hours at room temperature, the reaction mixture was poured on ice, made alkaline with ammonia, and the precipitate formed was purified by chromatography on silica gel (eluting agent: methylene chloride/ethanol 19:1). After evaporation, the residue was crystallized by trituration with a mixture of acetone and ether.

Yield: 0.5 gm (53% of theory).
M.p.: 173°-180° C.

EXAMPLE 32

2-(1-Phenyl-2-propyl)-5(6)-(5-methyl-3-oxo-4,5-dihydro-2H-6-pyridazinyl)-benzimidazole hydrochloride 5.1 gm of 5-methyl-6-[3-amino-4-(3-phenyl-isobutyryl-amino)-phenyl]-4,5-dihydro-2H-pyridazine-3-one were refluxed in 100 ml of glacial acetic acid for 1.5 hours. The glacial acetic acid was distilled off, and the residue was taken up in a mixture of ethanol and acetone. The hydrochloride was precipitated by addition of ethereal hydrochloric acid and obtained in crystalline form by trituration with a mixture of ether and ethanol.

Yield: 2.4 gm (45% of theory).
M.p.: 235°-239° C.

EXAMPLE 33

2-Cycloheptyl-5(6)-(5-methyl-3-oxo-4,5-dihydro-2H-6-pyridazinyl)-benzimidazole hydrochloride Prepared analogous to Example 32 from 5.5 gm of 5-methyl-6-(3-amino-4-cycloheptylcarbonylamino-phenyl)-4,5-dihydro-2H-pyridazine-3-one.

Yield: 4.2 gm (73% of theory).
M.p.: 255°-259° C.

EXAMPLE 34

2-(4-Hydroxyphenyl)-5(6)-(5-methyl-3-oxo-4,5-dihydro-2H-6-pyridazinyl)-benzimidazole hydrochloride Prepared analogous to Example 32 from 6.3 gm of 5-methyl-6-[3-amino-4-(4-hydroxy-benzoylamino)-phenyl]-4,5-dihydro-2H-pyridazine-3-one.

Yield: 4.4 gm (66% of theory).
M.p.: 350°-354° C.

EXAMPLE 35

2-(4-n-Hexyloxy-phenyl)-5(6)-(5-methyl-3-oxo-4,5-dihydro-2H-6-pyridazinyl)-benzimidazole hydrochloride Prepared analogous to Example 32 from 5.7 gm of 5-methyl-6-[3-amino-4-(4-n-hexyloxy-benzoyl-amino)-phenyl]-4,5-dihydro-2H-pyridazine-3-one.

Yield: 3.55 gm (60% of theory.
M.p.: 278°-282° C.

EXAMPLE 36

2-(3,4,5-Trimethoxy-phenyl)-5(6)-(5-methyl-3-oxo-4,5-dihydro-2H-pyridazinyl)-benzimidazole Prepared analogous to Example 32 from 14.9 gm of 5-methyl-6-[3-amino-4-(3,4,5-trimethoxy-benzoylamino)-phenyl]-4,5-dihydro-2H-pyridazine-3-one. The residue remaining after evaporation of the glacial acetic acid was extracted with boiling ethanol. After evaporation of the ethanol and stirring with ether, the substance was obtained in crystalline form.

Yield: 9.2 gm (65% of theory).
M.p.: 295°–300° C.

EXAMPLE 37

1-(3-Methyl-butyl)-2-methyl-5-(5-methyl-3-oxo-4,5-dihydro-2H-6-pyridazinyl)-benzimidazole (a) 5-Methyl-6-{3-amino-4-[N-acetyl-N-(3-methyl-butyl)-amino]-phenyl}-4,5-dihydro-2H-pyridazine-3-one 6 gm of 5-methyl-6-{3-nitro-4-[N-acetyl-N-(3-methyl-butyl)-amino]-phenyl}-4,5-dihydro-2H-pyridazine-3-one were dissolved in 150 ml of ethanol. 4 gm of Raney-nickel and 3 ml of 98% hydrazine hydrate were added, and the solution was stirred for 30 minutes at room temperature. The catalyst was filtered off, the filtrate was evaporated, and the residue was processed further without further purification.

(b) 1-(3-Methyl-butyl)-2-methyl-5-(5-methyl-3-oxo-4,5-dihydro-2H-6-pyridazinyl)-benzimidazole Prepared analogous to Example 32 from the product obtained according to (a). The product was purified by chromatography on silicagel (eluting agent: methylene chloride/ethanol=9:1).

Yield: 2.2 gm (43% of theory).
M.p.: 247° C.

EXAMPLE 38

1-Benzyl-2-trifluoromethyl-5-(5-methyl-3-oxo-4,5-dihydro-2H-6-pyridazinyl)-benzimidazole Prepared analogous to Example 28 from 5.2 gm of 5-methyl-6-(3-nitro-4-benzylamino-phenyl]-4,5-dihydro-2H-pyridazine-3-one.

Yield: 1.4 gm (23% of theory).
M.p.: 210°–212° C.

EXAMPLE 39

2-Methyl-5(6)-(5-ethyl-3-oxo-4,5-dihydro-2H-6-pyridazinyl)-benzimidazole

Prepared analogous to Example 31 from 1.2 gm of 5-ethyl-6-(3-nitro-4-amino-phenyl)-4,5-dihydro-2H-pyridazine-3-one.

Yield: 0.5 gm (41% of theory).
M.p.: 291°–295° C.

EXAMPLE 40

2-(4-Methoxy-phenyl)-5(6)-(5-ethyl-3-oxo-4,5-dihydro-2H-6-pyridazinyl)-benzimidazole hydrochloride Prepared analogous to Example 32 from 3.6 gm of 5-ethyl-6-[3-amino-4-(4-methoxy-benzoylamino)-phenyl]-4,5-dihydro-2H-pyridazine-3-one.

Yield: 3.6 gm (91% of theory).
M.p.: 192°–198° C.

EXAMPLE 41

2-(3-Methoxy-phenyl)-5(6)-(5-methyl-3-oxo-4,5-dihydro-2H-6-pyridazinyl)-benzimidazole Prepared analogous to Example 32 from 2.2 gm of 5-methyl-6-[3-amino-4-(3-methoxy-benzoylamino)-phenyl]-4,5-dihydro-2H-pyridazine-3-one and purification by means of chromatography on silicagel (eluting agent: methylene chloride/ethanol=19:1).

Yield: 0.72 gm (34% of theory).
M.p.: 295°–298° C.

EXAMPLE 42

2-(2-Bromo-5-methoxy-phenyl)-5(6)-(5-methyl-3-oxo-4,5-dihydro-2H-6-pyridazinyl)-benzimidazole Prepared analogous to Example 41 from 2.8 gm of 5-methyl-6-[3-amino-4-(2-bromo-5-methoxy-benzoylamino)-phenyl]-4,5-dihydro-2H-pyridazine-3-one.

Yield: 0.75 gm (28% of theory).
M.p.: sintering from 70° C.

EXAMPLE 43

2-Undecyl-5(6)-(5-methyl-3-oxo-4,5-dihydro-2H-6-pyridazinyl)-benzimidazole (a) 5-Methyl-6-(3-amino-4-undecane carbonylamino-phenyl)-4,5-dihydro-2H-pyridazine-3-one 10 gm of 5-methyl-6-(3-nitro-4-undecane carbonylamino-phenyl)-4,5-dihydro-2H-pyridazine-3-one were dissolved in 100 ml of dimethylformamide, and the solution was treated in the presence of 1 gm of 10% palladium charcoal with hydrogen for 1.2 hours at a pressure of 5 bar. After filtering off of the catalyst, the mixture was poured on ice and extracted with methylene chloride, and the organic phase was evaporated. The oily residue was further processed directly.

(b) 2-Undecyl-5(6)-(5-methyl-3-oxo-4,5-dihydro-2H-6-pyridazinyl)-benzimidazole

The product obtained according to (a) was dissolved in 100 ml of glacial acetic acid and refluxed for 1 hour. The solution was evaporated to about half of the original volume, poured on ice, and made alkaline with ammonia. The precipitated product was recrystallized from ethyl acetate. A further fraction was obtained by chromatographic purification of the mother liquors (silicagel, eluting agent: methylene chloride/ethanol=19:1).

Yield: 7.7 gm (87% of theory).
M.p.: 165°–169° C. (decomp.).

EXAMPLE 44

2-Methyl-5(6)-(5-n-butyl-3-oxo-4,5-dihydro-2H-6-pyridazinyl)-benzimidazole

Prepared analogous to Example 28 from 4 gm of 5-n-butyl-6-(3-nitro-4-amino-phenyl)-4,5-dihydro-2H-pyridazine-3-one.

Yield: 1.7 gm (43% of theory).
M.p.: 134°–136° C. (decomp.).

EXAMPLE 45

2-(4-methoxy-phenyl)-5(6)-(5-n-butyl-3-oxo-4,5-dihydro-2H-6-pyridazinyl)-benzimidazole hydrochloride Prepared analogous to Example 41 from 4.2 gm of 5-n-butyl-6-[3-amino-4-(4-methoxy-benzoylamino)-phenyl]-4,5-dihydro-2H-pyridazine-3-one. The hydrochloride was precipitated from ethyl acetate with ethereal hydrochloric acid.

Yield: 3.2 gm (73% of theory).
M.p.: 180°-190° C.

EXAMPLE 46

2-(1-Phenyl-1-ethyl)-5(6)-(5-methyl-3oxo-4,5-dihydro-2H-6-pyridazinyl)-benzimidazole hydrochloride Prepared analogous to Example 32 from 3 gm of 5-methyl-6-[3-amino-4-(2-phenyl-propionylamino)-phenyl]-4,5-dihydro-2H-pyridazine-3-one.
Yield: 1.6 gm (51% of theory).
M.p.: sintering from 85° C.

EXAMPLE 47

2-Ethoxy-5(6)-(5-methyl-3-oxo-4,5-dihydro-2H-6-pyridazinyl)-benzimidazole hydrochloride 10.9 gm of 5-methyl-6-(3,4-diamino-phenyl)-4,5-dihydro-2H-pyridazine-3-one were suspended in 12.5 gm of orthocarbonic acid tetraethyl ester. 10 ml of dimethylsulfoxide were added, and the mixture was refluxed for 1.5 hours. The solvent was distilled off, and the oily residue was crystallized by trituration with ether/chloroform. The hydrochloride was precipitated from acetone/ethanol (1:1) with ethereal hydrochloric acid and recrystallized from ethanol/isopropanol.
Yield: 7.6 gm (49% of theory).
M.p.: above 300° C.

EXAMPLE 48

2-(4-Methoxy-phenyl)-5(6)-(5-methyl-3-oxo-4,5-dihydro-2H-6-pyridazinyl)-benzimidazole hydrochloride 0.34 gm of sodium methylate were added to a suspension of 1.1 gm of 2-(4-hydroxy-phenyl)-5-(5-methyl-3-oxo-4,5-dihydro-2H-6-pyridazinyl)-benzimidazole hydrochloride in 50 ml of methanol. After a clear solution had formed, 2.52 gm of dimethylsulfate and another 0.34 gm of sodium methylate were added in portions. The overall reaction time was 6 hours at room temperature. The reaction mixture was poured on ice and then neutralized, and the precipitate formed thereby was purified on a silicagel column (eluting agent: methylene chloride/ethanol 50:1 to 25:1). The hydrochloride was precipitated from methanol with ethereal hydrochloric acid.
Yield: 0.59 gm (52% of theory).
M.p.: 311° C. (decomp.).

EXAMPLE 49

2-(4-Methoxy-phenyl)-5(6)-(5-methyl-3-oxo-4,5-dihydro-2H-6-pyridazinyl)-benzimidazole hydrochloride (a) 5-Methyl-6-[3-amino-4-(4-methoxy-benzoylamino)-phenyl]-4,5-dihydro-2H-pyridazine-3-one 203 gm of 5-methyl-6-[3-nitro-4-(4-methoxy-benzoylamino)-phenyl]-4,5-dihydro-2H-pyridazine-3-one were dissolved in 1.7 liters of dimethylformamide, and the solution was treated with hydrogen in the presence of 20 gm of 10% palladium charcoal for 2 hours at a pressure of 5 bar. After filtering off the catalyst, the filtrate was poured into 7.5 liters of ice water. The precipitated product was dried at 120° C.
Yield: 182 gm (97% of theory).
M.p.: 253° C.

(b) 2-(4-Methoxy-phenyl)-5(6)-(5-methyl-3-oxo-4,5-dihydro-2H-6-pyridazinyl)-benzimidazole hydrochloride 180 gm of 5-methyl-6-[3-amino-4-(4-methoxy-benzoylamino)-phenyl]-4,5-dihydro-2H-pyridazine-3-one were suspended in 1.5 liters of glacial acetic acid, and the suspension was refluxed for 30 minutes. After distilling off of 350 ml of the solvent at reduced pressure, the remaining mixture was treated with activated charcoal at 70° C. and filtered. After cooling to 20° C., the filtrate was added dropwise to a mixture of 2 liters of ice water and 1.5 liters of concentrated ammonia while stirring. By addition of more ice the temperature was kept below 20° C. The precipitated product was washed with water and dried at 80° C. By dissolution in isopropanol, mixing with concentrated hydrochloric acid and dilution with 2 liters of acetone the base was converted into the hydrochloride. The free base still contained in the motherliquors was treated correspondingly.
Yield: 176 gm (93% of theory).
M.p.: 300°-306° C. (decomp.).

EXAMPLE 50

2-(4-Methoxy-phenyl)-5(6)-(5-methyl-3-oxo-4,5-dihydro-2H-6-pyridazinyl)-benzimidazole hydrochloride 0.22 gm of 5-methyl-6-(3,4-diamino-phenyl)-4,5-dihydro-2H-pyridazine-3-one and 0.2 gm of 4-methoxy-benzamidine hydrochloride were triturated with each other, and the mixture was heated at 160° C. for 40 minutes. The reaction mixture was purified by chromatography on silicagel (eluting agent: methylene chloride/ethanol 50:1 to 25:1), and the hydrochloride was precipitated from methanol with ethereal hydrochloric acid.
Yield: 0.04 gm (10% of theory).
M.p.: 305°-307° C. (decomp.).

EXAMPLE 51

2-(4-Methoxy-phenyl)-5(6)-(5-methyl-3-oxo-4,5-dihydro-2H-6-pyridazinyl)-benzimidazole hydrochloride A mixture of 0.22 gm of 5-methyl-6-(3,4-diamino-phenyl)-4,5-dihydro-2H-pyridazine-3-one, 0.15 gm of 4-methoxy-benzonitrile and 0.17 gm of p-toluene sulfonic acid was heated for 30 minutes at 160° C. The reaction mixture was further processed analogous to Example 29.
Yield: 0.06 gm (16% of theory).
M.p.: 304°-309° C. (decomp.).

EXAMPLE 52

2-(4-Methoxy-phenyl)-5(6)-(4-methyl-3-oxo-4,5-dihydro-2H-6-pyridazinyl)-benzimidazole hydrochloride Prepared analogous to Example 51 with 0.22 gm of potassium tert. butylate instead of p-toluene sulfonic acid.
Yield: 0.03 gm (8% of theory).
M.p.: 305°-306° C. (decomp.).

EXAMPLE 53

2-(4-Methoxy-phenyl)-5(6)-(5-methyl-3-oxo-4,5-dihydro-2H-6-pyridazinyl)-benzimidazole hydrochloride A mixture of 0.22 gm of 5-methyl-6-(3,4-diamino-phenyl)-4,5-dihydro-2H-pyridazine-3-one and 0.42 gm of S-methyl-4-methoxy-thiobenzoic acid morpholide iodide was heated in 3 ml of ethylene glycol for 10 minutes at 140° C. After cooling, the mixture was poured into ice water, and the precipitated product was taken up in ether and purified analogous to Example 51.
Yield: 0.13 gm (35% of theory).
M.p.: 309°-311° C. (decomp.).

EXAMPLE 54

2-(4-Methoxy-phenyl)-5(6)-(5-methyl-3-oxo-4,5-dihydro-2H-6-pyridazinyl)-benzimidazole hydrochloride A mixture of 0.22 gm of 5-methyl-6-(3,4-diamino-phenyl)-4,5-dihydro-2H-pyridazine-3-one and 0.29 gm of 4-methoxy-benzoic acid phenyl ester was heated for 30 minutes at 150° C. The reaction mixture was further processed analogous to Example 51.

Yield: 0.23 gm (62% of theory).

M.p.: 108°-111° C. (decomp.).

The following examples illustrate a few pharmaceutical dosage unit compositions comprising a compound of the present invention as an active ingredient and represent the best modes contemplated of using the invention.

EXAMPLE 55

Tablets containing 100 mg of
2-(4-methoxy-phenyl)-5(6)-(5-methyl-3-oxo-4,5-dihydro-2N-6-pyridazinyl)-benzimidazole hydrochloride

| Composition: 1 tablet contains: | |
|---|---|
| Active ingredient | 100.0 mg |
| Lactose | 50.0 mg |
| Polyvinylpyrrolidone | 5.0 mg |
| Carboxymethylcellulose | 19.0 mg |
| Magnesium stearate | 1.0 mg |
| | 175.0 mg |

METHOD OF PREPARATION

The active ingredient was admixed with the lactose, and the mixture was homogeneously moistened with an aqueous 10% solution of the polyvinylpyrrolidone. The moist mixture obtained was granulated through a screen of 1.5 mm mesh size, dried in a circulation air drier at 50° C., and then passed through a screen of 1.0 mm mesh size. The granulate, the carboxymethylcellulose, and the magnesium stearate were mixed and compressed into 175 mg-tablets.

EXAMPLE 56

Coated tablets containing 50 mg of
2-(4-methoxy-phenyl)-5(6)-(5-methyl-3-oxo-4,5-dihydro-2H-6-pyridazinyl)-benzimidazole hydrochloride

| 1 coated tablet core contains: | |
|---|---|
| Active ingredient | 50.0 mg |
| Corn starch | 20.0 mg |
| Soluble starch | 2.0 mg |
| Carboxymethylcellulose | 7.0 mg |
| Magnesium stearate | 1.0 mg |
| | 80.0 mg |

METHOD OF PREPARATION

The active ingredient was admixed with the corn starch, and the mixture was homogeneously moistened with an aqueous solution of the soluble starch. The moist mixture obtained was granulated through a screen of 1.0 mm mesh size, dried in a circulation air drier at 50° C., and then passed through the same size screen. The granulate and the remaining auxiliary products were admixed and compressed into 80 mg cores. The finished cores were covered with a sugar coating in conventional manner.

EXAMPLE 57

Suppositories containing 75 mg of
2-(4-methoxy-phenyl)-5(6)-(5-methyl-3-oxo-4,5-dihydro-2H-6-pyridazinyl)-benzimidazole hydrochloride

| 1 Suppository contains: | |
|---|---|
| Active ingredient | 75.0 mg |
| Suppository base (e.g. cocoa butter) | 1,625.0 mg |
| | 1,700.0 mg |

METHOD OF PREPARATION

The suppository base was melted. At 38° C. the pulverized active ingredient was homogeneously dispersed in the melt. The suppository base was cooled to 35° C. and then poured into pre-cooled molds. The weight of the suppository was 1.7 g.

EXAMPLE 58

Ampules containing 50 mg of
2-(4-methoxy-phenyl)-5(6)-(5-methyl-3-oxo-4,5-dihydro-2H-6-pyridazinyl)-benzimidazole hydrochloride

| 1 Ampule contains: | | |
|---|---|---|
| Active ingredient | | 50.0 mg |
| Sorbitol | | 250.0 mg |
| Distilled water | q.s.ad | 5 ml |

METHOD OF PREPARATION

The active ingredient and sorbitol were dissolved in distilled water, and the mixture obtained was made up to the given volume and sterile-filtered.

EXAMPLE 59

Drop solution containing 25 mg/5 ml of
2-(4-methoxy-phenyl)-5(6)-(5-methyl-3-oxo-4,5-dihydro-2H-6-pyridazinyl)-benzimidazole hydrochloride

| Active ingredient | | 5.0 gm |
|---|---|---|
| Methyl p-oxybenzoate | | 0.035 gm |
| Propyl p-oxybenzoate | | 0.015 gm |
| Aniseed oil | | 0.05 gm |
| Menthol | | 0.06 gm |
| Saccharin sodium | | 1.0 gm |
| Glycerin | | 10.0 gm |
| Ethanol | | 40.0 gm |
| Distilled water | q.s.ad | 100.0 gm |

METHOD OF PREPARATION

The methyl and propyl p-oxybenzoates were dissolved in ethanol, and the aniseed oil and methol were added thereto. Subsequently, the active ingredient, glycerin, and saccharin sodium were dissolved in water, and the solution obtained was added to the first solution. The combined solutions were sterile-filtered.

Any one of the other compounds embraced by formula I or a no-toxic, pharmaceutically acceptable acid addition salt thereof may be substituted for the particular active ingredient in Examples 55 through 59. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

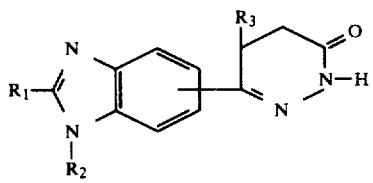

wherein $R_1$ is hydrogen; trifluoromethyl; alkyl of 1 to 11 carbon atoms; cycloalkyl of 3 to 7 carbon atoms; hydroxyl; alkoxy of 1 to 6 carbon atoms; mercapto; (alkyl of 1 to 6 carbon atoms)-mercapto; phenyl(alkyl of 1 to 3 carbon atoms); phenyl; or mono-, di- or trisubstituted phenyl, where the substituents, which may be identical to or different from each other, are each halogen, alkyl of 1 to 4 carbon atoms, (alkyl of 1 to 6 carbon atoms)sulfinyl, hydroxyl, alkoxy of 1 to 6 carbon atoms, mercapto or (alkyl of 1 to 6 carbon atoms)-mercapto;

$R_2$ is hydrogen, alkyl of 1 to 6 carbon atoms, cycloalkyl of 3 to 6 carbon atoms or phenyl-(alkyl of 1 to 3 carbon atoms); and $R_3$ is alkyl of 1 to 6 carbon atoms;

an optically active antipode thereof; or a non-toxic, pharmaceutically acceptable acid addition salt of said compound or of said optically active antipode.

2. A compound of claim 1 where $R_1$ is hydrogen, trifluoromethyl; alkyl of 1 to 11 carbon atoms; cycloalkyl of 3 to 7 carbon atoms; hydroxyl; alkoxy of 1 to 6 carbon atoms; mercapto; (alkyl of 1 to 6 carbon atoms)-mercapto; phenyl-(alkyl of 1 to 3 carbon atoms); phenyl; hydroxyphenyl; halo-phenyl; (alkyl of 1 to 4 carbon atoms)-phenyl; (alkoxy of 1 to 6 carbon atoms)-phenyl; methoxy-halo-phenyl; methylmercaptophenyl; methylsulfinyl-phenyl; dimethoxy-phenyl; methoxy-methylmercapto-phenyl; methoxy-methylsulfinyl-phenyl; or trimethoxy-phenyl;

$R_2$ is hydrogen, alkyl of 1 to 5 carbon atoms, cyclopropyl, cyclohexyl or benzyl; and $R_3$ is alkyl of 1 to 4 carbon atoms;

an optically active antipode thereof; or a non-toxic, pharmaceutically acceptable acid addition salt of said compound or of said optically active antipode.

3. A compound of claim 1, where $R_1$ is hydrogen, methyl, isopropyl, n-pentyl, 2-pentyl, n-hexyl, n-undecyl, cyclopropyl, cyclohexyl, cycloheptyl, hydroxy, ethoxy, mercapto, methylmercapto, isopropyl-mercapto, n-hexylmercapto, trifluoromethyl, 1-phenyl-ethyl, 1-phenyl-2-propyl, phenyl, 2-fluorophenyl, 4-hydroxy-phenyl, 2-methoxy-phenyl, 3-methoxy-phenyl, 4-methoxy-phenyl, 2,4-dimethoxy-phenyl, 3,4-dimethoxy-phenyl, 3,4,5-trimethoxy-phenyl, 4-n-hexyloxy-phenyl, 4-methyl-phenyl, 4-tert. butyl-phenyl, 4-chlorophenyl, 2-methoxy-4-methylmercapto-phenyl, 2-methoxy-4-methylsulfinyl-phenyl, or 2-bromo-5-methoxy-phenyl;

$R_2$ is hydrogen, methyl, 3-methyl-butyl, cyclopropyl, cyclohexyl, or benzyl; and $R_3$ is methyl, ethyl, or n-butyl;

an optically active antipode thereof; or a non-toxic, pharmaceutically acceptable acid addition salt of said compound or of said optically active antipode.

4. A compound of claim 1 where $R_1$ is hydrogen, methyl, 2-pentyl, cyclopropyl, 1-phenyl-ethyl, ethoxy, methyl-mercapto, trifluoromethyl, phenyl, 4-methyl-phenyl, 2-fluorophenyl, 3-methoxy-phenyl, 4-methoxy-phenyl, 4-hexyloxyphenyl, or 4-hydroxy-phenyl;

$R_2$ is hydrogen, 3-methyl-butyl, cyclopropyl or benzyl; and $R_3$ is methyl;

an optically active antipode thereof; or a non-toxic, pharmaceutically acceptable acid addition salt of said compound or of said optically active antipode.

5. A compound of claim 1, where p1 $R_1$ is methyl, trifluoromethyl, 4-methyl-phenyl, 1-phenyl-ethyl, 2-fluoro-phenyl, 3-methoxy-phenyl, 4-methoxy-phenyl or 4-hydroxy-phenyl;

$R_2$ is hydrogen; and $R_3$ is methyl;

an optically active antipode thereof; or a non-toxic, pharmaceutically acceptable acid addition salt of said compound or of said optically active antipode.

6. A compound of claim 1, which is 2-(4-methoxy-phenyl)-5(6)-(5-methyl-3-oxo-4,5-dihydro-2H-6-pyridazinyl)-benzimidazole, an optically active antipode thereof, or a non-toxic, pharmaceutically acceptable acid addition salt thereof.

7. A compound of claim 1, which is 1-(3-methyl-butyl)-2-methyl-5-(5-methyl-3-oxo-4,5-dihydro-2H-6-pyridazinyl)-benzimidazole, an optically active antipode thereof, or a non-toxic, pharmaceutically acceptable acid addition salt thereof.

8. A compound of claim 1, which is 2-(4-methyl-phenyl)-5(6)-(5-methyl-3-oxo-4,5-dihydro-2H-6-pyridazinyl)-benzimidazole, an optically active antipode thereof, or a non-toxic, pharmaceutically acceptable acid addition salt thereof.

9. A cardiotonic or antithrombotic pharmaceutical composition consisting essentially of an inert pharmaceutical carrier and an effective cardiotonic or antithrombotic amount of a compound of claim 1.

10. The method of increasing the strength of myocardial contraction or preventing or relieving thrombosis in a warm-blooded animal in need thereof, which comprises perorally or parenterally administering to said animal a composition of claim 9.

* * * * *